(12) United States Patent
Yu et al.

(10) Patent No.: US 8,163,477 B2
(45) Date of Patent: Apr. 24, 2012

(54) NUCLEASE-BASED METHOD FOR DETECTING AND QUANTITATING OLIGONUCLEOTIDES

(75) Inventors: Zhengrong Yu, Carlsbad, CA (US); Brenda F. Baker, Carlsbad, CA (US); Hongjiang Wu, Carlsbad, CA (US)

(73) Assignee: Isis Pharmaceuticals, Inc, Carlsbad, CA (US)

( * ) Notice: Subject to any disclaimer, the term of this patent is extended or adjusted under 35 U.S.C. 154(b) by 712 days.

(21) Appl. No.: 10/445,996

(22) Filed: May 27, 2003

(65) Prior Publication Data

US 2004/0005618 A1    Jan. 8, 2004

Related U.S. Application Data

(63) Continuation-in-part of application No. 09/705,587, filed on Nov. 3, 2000, now abandoned.

(51) Int. Cl.
  *C07H 21/04* (2006.01)
  *C12Q 1/68* (2006.01)
(52) U.S. Cl. ...... 435/6.1; 435/6.11; 435/6.12; 536/23.1; 536/24.3
(58) Field of Classification Search .......... None
  See application file for complete search history.

(56) References Cited

U.S. PATENT DOCUMENTS

| | | | | |
|---|---|---|---|---|
| 5,945,290 | A * | 8/1999 | Cowsert .......................... | 435/6 |
| 6,228,578 | B1 * | 5/2001 | Impraim et al. .................. | 435/6 |
| 6,573,048 | B1 * | 6/2003 | VanAtta et al. ................... | 435/6 |
| 6,900,013 | B1 * | 5/2005 | Wang et al. ....................... | 435/6 |

FOREIGN PATENT DOCUMENTS

WO    WO 00/56926    9/2000

OTHER PUBLICATIONS

Temsami (Analytical Biochemistry, vol. 215, p. 54-58, 1993).*
Boutet et al. (Biochemical and Biophysical Res. Comm., vol. 268, pp. 92-98, Feb. 2000).*
de Serres et al (Analytical Biochemistry, vol. 233, pp. 228-233, 1996).*
Lind et al (Nucleic Acids Research vol. 26, No. 16, pp. 3694-3699, 1998).*
Prosnyak et al (Genomics, vol. 21, p. 490-494, 1994).*
Lundin (Nucleic Acids Research, vol. 25, No. 12, p. 2535-2536; 1997).*
Bigelow et al., "High-performance liquid chromatographic analysis of phosphorothioate analogues of oligodeoxynucleotides in biological fluids", *J. Chromatography* 1990 533:133-140.
Bourque et al., "Quantitative analysis of phosphorothioate oligonucleotides in biological fluids using direct injection fast anion-exchange chromatography", *J. Chromatography* 1994 662:343-349.
Boutet et al., "Real-Time Monitoring of the Hybridization Reaction: Application to the Quantification of Oligonucleotides in Biological Samples", *Biochemical and Biophy. Res. Comm.* 2000 268:92-98.

(Continued)

*Primary Examiner* — Jeanine A Goldberg
(74) *Attorney, Agent, or Firm* — Woodcock Washburn

(57) ABSTRACT

A method for quantitating an oligonucleotide in a sample of bodily fluid and/or extract is provided. The method provides for the detection and/or localization of oligonucleotides, including administered modified oligonucleotides, for therapeutic and/or pharmacokinetic purposes.

14 Claims, 7 Drawing Sheets

OTHER PUBLICATIONS

Chen et al., "Determination of antisense phosphorothioate oligonucleotides and catabolites in biological fluids and tissue extracts using anion-exchange high-performance liquid chromatography", *J. Chromatography* 1997 692:43-51.

Cohen et al., "A Nonradioisotope Approach to Study In Vivo Metabolism of Phosphorothioate Oligonucleotides", *Antisense & Nucleic Acid Drug Dev.* 1997 7:13-22.

Deverre et al., "A competitive enzyme hybridization assay for plasma determination of phosphodiester and phosphorothioate antisense oligonucleotides", *Nucleic Acids Res.* 1997 25(18):3584-3589.

Geary et al., "A Nonradioisotope Biomedical Assay for Intact Oligonucleotide and Its Chain-Shortened Metabolites Used for Determination of Exposure and Elimination Half-Life of Antisense Drugs in Tissue", *Analytical Biochem.* 1999 274:241-248.

Kacian et al., "A rapid and sensitive chemiluminescent DNA probe system (HPA) for detection of amplified HIV and HBV DNA", *Fresenius J. Anal. Chem.* 1990 373:95.

Maier et al., "Quantitation of Phosphorothioate Oligonucleotides in Human Blood Plasma Using a Nanoparticle-Based Method for Solid-Phase Extraction", *Anal. Chem.* 1998 70:2197-2204.

Mendoza et al., "High-Throughput Microarray-Based Enzyme-Linked Immunosorbent Assay (ELISA)", *BioTechniques* 1999 27:778-788.

Reyderman et al., "Quantitative Determination of Short Single-Stranded Oligonucleotides from Blood Plasma Using Capillary Electrophoresis with Laser-Induced Fluorescence", *Anal. Chem.* 1997 69:3218-3222 6.

deSerres et al., "Development of a Novel Scintillation Proximity Competitive Hybridization Assay for the Determination of Phosphorothioate Antisense Oligonucleotides Plasma Concentrations in a Toxicokinetic Study", *Analytical Biochemistry* 1996 233:228-233.

Temsamani et al., "A Rapid Method for Quantitation of Oligodeoxynucleotide Phosphorothioates in Biological Fluids and Tissues", *Analytical Biochem.* 1993 215:54-58.

* cited by examiner

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 1
gctgattaga gagaggtccc            20

<210> SEQ ID NO 2
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 2
gcccaagctg gcatccgtca            20

```
<210> SEQ ID NO 3
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 3
tccagcactt tcttttccgg                                              20

<210> SEQ ID NO 4
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 4
gctccttcca ctgatcctgc                                              20
```

NUCLEASE-BASED METHOD FOR DETECTING AND QUANTITATING OLIGONUCLEOTIDES

INTRODUCTION

This application is a continuation-in-part of U.S. Ser. No. 09/705,587 filed Nov. 3, 2000 now abandoned.

FIELD OF THE INVENTION

The present invention is directed to a nuclease-based solid phase assay for detecting oligonucleotides in samples of bodily fluids and/or extracts.

BACKGROUND OF THE INVENTION

The detection of specific nucleic acid sequences is commonplace in the research laboratory. Southern (*J. Mol. Biol.* 1975.98:503-527) teaches detection of specific sequences among DNA fragments separated by gel electrophoresis using "blotting" or transfer of the DNA fragments to a membrane, followed by hybridization of denatured DNA fragments with radioactive probes and autoradiography. This procedure has been extended to the detection of RNA molecules extracted from cells or tissues ("Northern" blotting). Further improvements have involved faster and more quantitative "dot-blotting" procedures to detect DNA or RNA from tissues or cells.

Other methods are used to detect and characterize specific nucleic acid sequences and sequence changes. These methods must be able to create detectable signals from a very low copy number of the sequence of interest. Nucleic acids detection methods include capillary gel electrophoresis (CGE) (U.S. Pat. No. 5,420,265) and signal amplification technology such as the polymerase chain reaction (PCR) (U.S. Pat. Nos. 4,683,195 and 4,683,202) and ligase chain reaction (LCR) (Barany, *Proc. Natl. Acad. Sci.* 1991.88:189).

Recently, considerable interest has been generated in the development of synthetic antisense oligonucleotides as therapeutic agents. These antisense molecules and strategies for their use have been reviewed by Agarwal (*Trends in Biotechnology* 1991.10:152-158) and Crooke (*Antisense Research and Applications*, Chapter 1, Basic Principles of Antisense Therapeutics, Springer-Verlag Press, New York, 1998). For an antisense therapeutic to be effective, the oligonucleotide must be administered to a patient and must reach the specific nucleic acid target for which it was designed. Consequently, there is a need to be able to detect oligonucleotides in bodily fluids and extracts. In animal models, radiolabeled oligonucleotides have been administered to the subject and the distribution of the oligonucleotides within the body has been assessed by extraction of the oligonucleotides followed by autoradiography (Agarwal et al. *Proc. Natl. Acad. Sci.* 1991.88:7595-7599). A common aspect of current procedures is the detection of large DNA or RNA molecules (>100 bp). Impraim et al. (U.S. Pat. No. 6,228,578) describe a non-radioactive hybridization assay and kit for detection of genetic defects, microbial infections or viral infections by detecting large pieces of nucleic acid molecules. The method has several prescribed steps, the first being hydrolyzing the RNA in the sample and denaturing the target DNA that is to be detected. Next, the target DNA sequence is hybridized to a complementary RNA probe to form a double-stranded DNA/RNA hybrid, which is followed by capture of the hybrid onto a solid phase where an anti-hybrid antibody has been immobilized. The non-hybridized probe is eliminated by digestion with Rnase and the bound hybrid is then detected. This method does not, however, allow for detection of small molecules such as antisense compounds 20 to 30 nucleobases in length but instead is for detection of nucleic acid molecules from organisms such as human papilloma virus and hepatitis B virus. Further, because the method is designed for detection of much larger nucleic acid molecules, its sensitivity is limited; this is because the molar sensitivity of a method is dependent on the molecular weight of the entities being detected.

Thus, the small size (20-30 bp) of oligonucleotides used for antisense therapeutics presents unique concerns for design of detection methods, such as, for example, nonspecific binding or the absence of binding to probes producing false negatives/positives. Temsamani et al. (1993) disclose a method for quantitation and detection of phosphorothioate modified oligonucleotides. In this method, oligonucleotides are first extracted from tissues and body fluids and then the first step is explicitly stated to be immobilization of an oligonucleotide to a solid support, specifically a nylon membrane. The membrane-bound oligonucleotide is then hybridized with a radioactive-labeled complementary oligonucleotide and exposed to x-ray film, or alternatively, hybridized with a probe that is chemiluminescent, either method of hybridization allowing for detection of the bound oligonucleotide. This method, however, does not employ any method for removal of non-hybridized probe, such as with a nuclease, a step that would enhance the sensitivity of the assay by decreasing the amount of noise. In fact, the detection of oligonucleotides using this assay is reported to be in the range of only as low as 1.5 nanograms There is a need for more sensitive methods for detecting administered modified oligonucleotide compounds, such as antisense therapeutics, methods with sensitivity below the nanogram range. Highly sensitive methods would be useful for determining the concentrations of modified oligonucleotide therapeutics in animal models and/or in the clinic. Further uses would be to study the pharmacokinetic properties of oligonucleotide therapeutics in animal models and/or in the clinic.

SUMMARY OF THE INVENTION

The present invention relates to methods for detecting oligonucleotides in bodily fluids and extracts. The methods are also useful for quantifying oligonucleotides and/or investigating the pharmacokinetics of oligonucleotides.

Thus, in a first aspect, the present invention features a method for screening a bodily fluid and/or extract for the presence of an oligonucleotide. Preferably, the oligonucleotide comprises one or more modifications to the backbone and/or nucleotide bases. In a preferred embodiment the sample of bodily fluid and/or extract is mammalian plasma, blood or serum, and more preferably the sample is a human plasma sample. Detection of the oligonucleotide is performed by contacting the sample of bodily fluid and/or extract with a labeled probe, wherein the probe comprises a detectable marker and a binding moiety that are covalently bound to the probe, placing the sample in contact with a solid support to which a binding partner of the binding moiety is attached so that the hybrid moieties attach to the solid support, removing oligonucleotide that has not formed a hybrid moiety from the sample, contacting the sample with a single strand-specific nuclease to degrade labeled, unhybridized probe, removing any unbound detectable marker from the sample, and detecting a label associated with the marker wherein the presence of the label indicates the presence of hybrid moieties bound to the solid support and the presence of antisense oligonucleotides in the sample at concentrations between about 50 and 1400 picomolar in the liquid sample.

Further aspects of the invention are described within the description of the preferred embodiments. The summary of the invention described above is not limiting and other features and advantages of the invention will be apparent from the following detailed description of the invention and from the claims.

DETAILED DESCRIPTION OF THE INVENTION

The present invention provides a highly sensitive method (in the picomolar range) for detecting oligonucleotides, particularly modified oligonucleotides, in a bodily fluid and/or extract. In the context of the present invention, an oligonucleotide is a small nucleic acid molecule that contains between 8 and 50 nucleobases, and in most cases is from 20 to 30 nucleobases in length. Current methods for detecting and or quantitating oligonucleotides such as capillary gel electrophoresis (CGE) provide increased detection of small molecules when compared to traditional slab-gel electrophoresis. CGE has been used for size-based separation of biological macromolecules such as DNA restriction fragments, proteins and oligonucleotides. The methods described herein provide a 500-1000 fold increase in the sensitivity of detection of oligonucleotides in biological samples when compared to methods such as CGE. The method of the present invention also provides for improvements in detection level sensitivity over methods in the literature that describe detection of modified oligonucleotides only in the nanogram range (Temsamani et al. 1993. *Anal. Biochem.* 215:54-58; Boutet et al. 2000. *Biochem. Biophys. Res. Commun.* 268:92-98).

The present method can be used, for example, to detect, localize and quantify administered oligonucleotides in bodily fluids and extracts taken from patients undergoing antisense oligonucleotide therapy. Further uses for this invention are for studying the pharmacokinetic properties of oligonucleotides in animal models and in humans.

Figure 1:
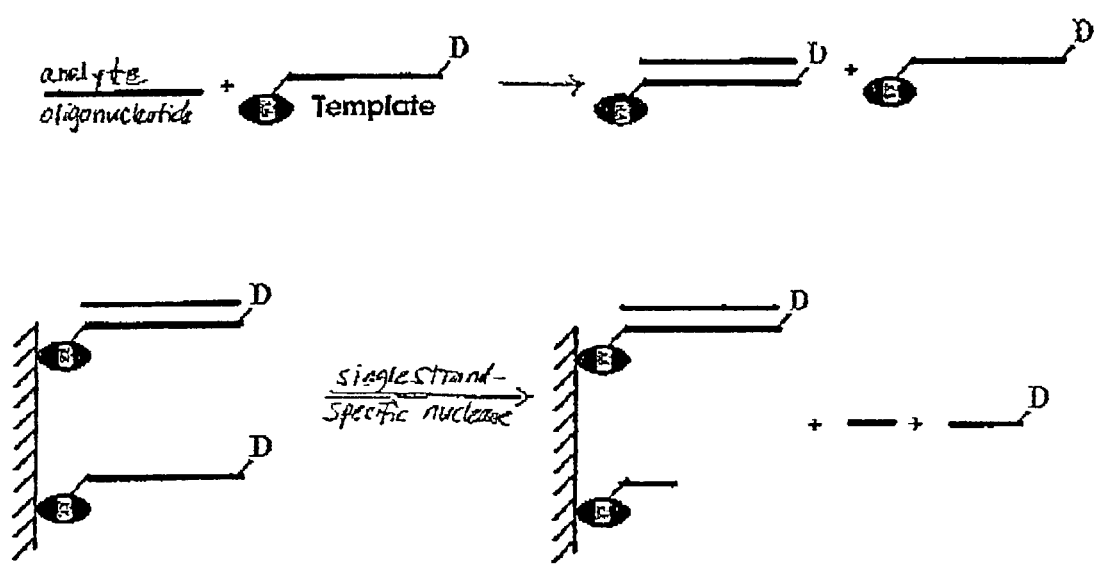
FIG. 1 is a schematic diagram showing the mechanism of the nuclease-based cutting assay of the present invention. B=binding moiety; D=detectable marker. The cross-hatched area represents a solid support coated with a compound to which the binding moiety binds.
Figure 2:
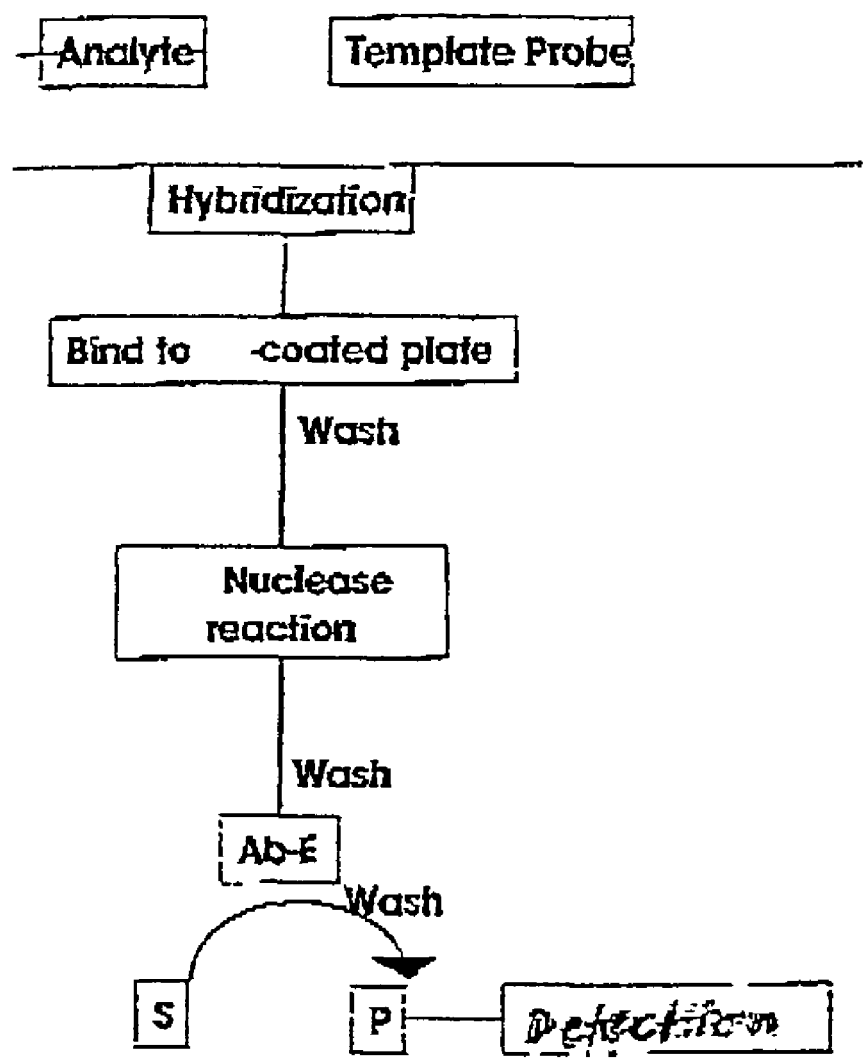
FIG. 2 is a schematic diagram showing the assay method of the present invention.

The oligonucleotide detection method of the present invention, referred to herein as the "cutting assay", is summarized in FIGS. 1 and 2. An oligonucleotide, preferably an oligonucleotide which has been administered to a subject, is detected by obtaining a sample of bodily fluid and/or extract from the subject and contacting the sample with a probe which has a sequence which is complementary to the administered oligonucleotide. Unlike previous methods for detection of DNA or nucleic acids (Impraim et al. U.S. Pat. No. 6,228,578), the method of the present invention is method that for the first time involves detection of nucleic acid molecules with a probe that has both binding and detection properties, through covalent binding of a detectable marker and a binding moiety. The probe of the present invention comprises a detectable marker and a binding moiety that are covalently bound to each other and which allows binding of the probe to a solid support to which the binding partner of the moiety is already bound. Solid supports include, for example, beads, culture dishes and 96-well plates. In a preferred embodiment, the detectable marker is digoxigenin which is incorporated into the probe using digoxigenin-labeled UTP (D-UTP), and the moiety which allows binding of the probe to the solid support is biotin which binds to a streptavidin-coated solid support.

Both the bound (probe+oligonucleotide analyte) and unbound probes bind to the solid support. A single strand-specific nuclease is then added to degrade the unhybridized probe and the solid support is washed to remove the degradation products. Examples of single strand-specific nucleases suitable for use in the present invention include S1 nuclease and mung bean nuclease. Thus, the only label detected is that of the probe-oligonucleotide analyte hybrid. Detection and quantitation are via the detectable marker's binding partner(s) and/or substrate(s). For example, an alkaline phosphatase-labeled anti-digoxigenin antibody is used to detect the bound digoxigenin-containing probe.

Although digoxigenin is exemplified herein as the detectable marker, the use of any detectable marker capable of being incorporated into an oligonucleotide probe is within the scope of the present invention. Various detectable markers have been discussed in the art and each marker has a well known protocol for its use and detection. Such protocols or approaches can include, but are not limited to, fluorometric measurement, autoradiographic measurement, colorimetric measurement, visual observation, chemiluminescent measurement, electrochemical measurement and the like.

Similarly, although the biotin-streptavindin system is used in the examples described herein, any suitable conjugate pair may be used to bind the probe to the solid support, including antibody-coated solid supports and antigen-conjugated probes.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such "modified" or substituted oligonucleotides are often preferred over native forms because of desirable properties such as, for example, enhanced cellular uptake, enhanced binding to target, increased stability in the presence of nucleases and an increase in bioavailability.

Within the concept of "modified" oligonucleotides, the present invention also includes detection of compositions employing oligonucleotide compounds which are chimeric compounds. "Chimeric" oligonucleotide compounds or "chimeras," in the context of this invention, are nucleic acid compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or consist of an oligomeric sequence known to modify complement activation. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate oligodeoxynucleotides hybridizing to the same target region. Cleavage of the RNA target can be routinely detected by gel electrophoresis and, if necessary, associated nucleic acid hybridization techniques known in the art. RNase H-mediated target cleavage is distinct from the use of ribozymes to cleave nucleic acids.

By way of example, such "chimeras" may be "gapmers," i.e., oligonucleotides in which a central portion (the "gap") of the oligonucleotide serves as a substrate for, e.g., RNase H, and the 5' and 3' portions (the "wings") are modified in such a fashion so as to have greater affinity for, or stability when duplexed with, the target RNA molecule but are unable to support nuclease activity (e.g., 2'-fluoro- or 2'-methoxyethoxy-substituted). Other chimeras include "hemimers," that is, oligonucleotides in which the 5' portion of the oligonucleotide serves as a substrate for, e.g., RNase H, whereas the 3' portion is modified in such a fashion so as to have greater affinity for, or stability when duplexed with, the target RNA molecule but is unable to support nuclease activity (e.g., 2'-fluoro- or 2'-methoxyethoxy-substituted), or vice-versa.

A number of chemical modifications to oligonucleotides that confer greater oligonucleotide:RNA duplex stability have been described by Freier et al. (*Nucl. Acids Res.*, 1997, 25, 4429). Such modifications are preferred for the RNase H-refractory portions of chimeric oligonucleotides and may generally be used to enhance the affinity of an antisense compound for a target RNA.

Chimeric modified oligonucleotide compounds may be formed as composite structures of two or more oligonucleotides, modified oligonucleotides, oligonucleosides and/or oligonucleotide mimetics as described above, ligand-oligonucleotide constructs, or complement protein-oligonucleotide constructs as described herein. Some of these compounds have also been referred to in the art as hybrids or gapmers. Representative United States patents that teach the preparation of some of these hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; 5,955,589 and 5,700,922, certain of which are commonly owned, and each of which is herein incorporated by reference.

Modifications to an oligonucleotide molecule can alter the concentration of the molecule required to elicit the effect for which the molecule is designed. Non limiting examples include varying the amount of phosphorothioate linkages in the oligonucleotide or altering the oligonucleotide base composition and chemistry such as in the preparation of CpG oligodeoxynucleotides as described by Krieg et al. *Nature* 1995.374:546-549, Weiner et al. *Proc. Natl. Acad. Sci. USA* 1997.94:10833-10837, Liu, H. M. et al. *Blood* 1998.15; 92(10):3730-3736, Boggs, R. T. et al., *Antisense Nucleic Acid Drug Dev.* 1997.7(5):461-471, and Kline et al. *J. Immunol* 1998.15; 160(6):2555-2559.

Also detectable by the methods of the invention are compositions employing oligonucleotides that are substantially chirally pure with regard to particular positions within the oligonucleotides. Examples of substantially chirally pure oligonucleotides include, but are not limited to, those having phosphorothioate linkages that are at least 75% Sp or Rp (U.S. Pat. No. 5,587,361) and those having substantially chirally pure (Sp or Rp) alkylphosphonate, phosphoramidate or phosphotriester linkages (U.S. Pat. Nos. 5,212,295 and 5,521,302).

Specific examples of some preferred modified oligonucleotides detectable by the present invention include those containing phosphorothioates (P=S oligonucleotides), phosphotriesters, methyl phosphonates, short chain alkyl or cycloalkyl intersugar linkages or short chain heteroatomic or heterocyclic intersugar linkages. Oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Examples of modified oligonucleotide backbones include phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, certain of which are commonly owned with this application, and each of which is herein incorporated by reference.

Additional examples of modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, certain of which are commonly owned with this application.

In other example oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262. Further teaching of PNA compounds can be found in Nielsen et al. *Science* 1991.254, 1497-1500.

Additional examples are oligonucleotides with phosphorothioate backbones and oligonucleosides with heteroatom backbones, and in particular —CH$_2$—NH—O—CH$_2$—, —CH$_2$—N(CH$_3$)—O—CH$_2$— [known as a methylene (methylimino) or MMI backbone], —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— [wherein the amide native phosphodiester backbone is represented as —O—P—O—CH$_2$—] of the above referenced U.S. Pat. No. 5,489,677, and the amide backbones of the above referenced U.S. Pat. No. 5,602,240. Oligonucleotides having morpholino backbone structures of the above-referenced U.S. Pat. No. 5,034,506, are also detectable using methods of the present invention.

Modified oligonucleotides may also contain one or more substituted sugar moieties. Example oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Non limiting examples are O[(CH$_2$)NO]m CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]2, where n and m are from 1 to about 10. Other examples comprise one of the following at the 2' position: C1 to C10 lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Other example modifications include 2'-methoxyethoxy (2'-O—CH$_2$CH$_2$OCH$_3$, also known as 2'-O-(2-methoxyethyl) or 2'-MOE) (Martin et al., *Helv. Chim. Acta,* 1995, 78, 486-504) i.e., an alkoxyalkoxy group. Modifications which include 2'-dimethylaminooxyethoxy, i.e., a O(CH$_2$)$_2$ON(CH$_3$)$_2$ group, also known as 2'-DMAOE, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$.

Additional example modifications include 2'-methoxy (2'-O—CH$_3$), 2'-aminopropoxy (2'-OCH$_2$CH$_2$CH$_2$NH$_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in *The Concise Encyclopedia Of Polymer Science And Engineering*, pages 858-859, Kroschwitz, J. I. ed. John Wiley & Sons 1990, those disclosed by Englisch et al. Angewandte Chemie, *International Edition* 1991.30, 613, and those disclosed by Sanghvi, Y. S., Chapter 15, *Antisense Research and Applications* pages 289-302, Crooke, S. T. and Lebleu, B. ed. *CRC Press* 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B. eds., *Antisense Research and Applications*, CRC Press, Boca Raton 1993. pp. 276-278).

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, certain of which are commonly owned with the instant application, and each of which is herein incorporated by reference, and U.S. Pat. No. 5,750,692, which is commonly owned with the instant application and also herein incorporated by reference.

Another modification of oligonucleotides detectable by the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al. *Proc. Natl. Acad. Sci. USA* 1989.86, 6553-6556), cholic acid (Manoharan et al. *Bioorg. Med. Chem. Let.* 1994.4:1053-1060), a thioether, e.g., hexyl-S-tritylthiol (Manoharan et al. *Ann. N.Y. Acad. Sci.* 1992.660:306-309; Manoharan et al. *Bioorg. Med. Chem. Let.* 1993.3:2765-2770), a thiocholesterol (Oberhauser et al. *Nucl. Acids Res.* 1992. 20:533-538), an aliphatic chain, e.g., dodecandiol or undecyl residues (Saison-Behmoaras et al., *EMBO J.* 1991.10:1111-1118; Kabanov et al. *FEBS Lett.* 1990.259:327-330; Svinarchuk et al. *Biochimie* 1993.75:49-54), a phospholipid, e.g., di-hexadecyl-rac-glycerol or triethylammonium 1,2-di-O-hexadecyl-rac-glycero-3-H-phosphonate (Manoharan et al. *Tetrahedron Lett.* 1995.36:3651-3654; Shea et al. *Nucl. Acids Res.* 1990.18: 3777-3783), a polyamine or a polyethylene glycol chain (Manoharan et al. *Nucleosides & Nucleotides* 1995.14:969-973), or adamantane acetic acid (Manoharan et al. *Tetrahedron Lett.* 1995.36:3651-3654), a palmityl moiety (Mishra et al. *Biochim. Biophys. Acta* 1995.1264:229-237), or an octadecylamine or hexylamino-carbonyl-oxycholesterol moiety (Crooke et al. *J. Pharmacol. Exp. Ther.* 1996.277:923-937).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide.

Further examples of modifications for the oligonucleotides detectable by the present invention involve chemically linking to the oligonucleotide one or more lipophilic moieties which enhance the cellular uptake of the oligonucleotide. Such lipophilic moieties may be linked to an oligonucleotide at several different positions on the oligonucleotide. Some non-limiting example positions include the 3' position of the sugar of the 3' terminal nucleotide, the 5' position of the sugar of the 5' terminal nucleotide, and the 2' position of the sugar of any nucleotide. The N6 position of a purine nucleobase may also be utilized to link a lipophilic moiety to an oligonucleotide of the invention (Gebeyehu, G. et al. *Nucleic Acids Res.* 1987.15:4513). Such lipophilic moieties include but are not limited to a cholesteryl moiety (Letsinger et al. *Proc. Natl. Acad. Sci. USA* 1989.86:6553), cholic acid (Manoharan et al. *Bioorg. Med. Chem. Let.* 1994.4:1053), a thioether, e.g., hexyl-S-tritylthiol (Manoharan et al. *Ann. N.Y. Acad. Sci.* 1992. 660: 306; Manoharan et al. *Bioorg. Med. Chem. Let.* 1993.3:2765), a thiocholesterol (Oberhauser et al. *Nucl. Acids Res.* 1992. 20:533), an aliphatic chain, e.g., dodecandiol or undecyl residues (Saison-Behmoaras et al. *EMBO J.* 1991.10:111; Kabanov et al. *FEBS Lett.* 1990.259:327; Svinarchuk et al. *Biochimie* 1993.75:49), a phospholipid, e.g., di-hexadecyl-rac-glycerol or triethylammonium 1,2-di-O-hexadecyl-rac-glycero-3-H-phosphonate (Manoharan et al. *Tetrahedron Lett.* 1995.36:3651; Shea et al. *Nucl. Acids Res.* 1990.18:3777), a polyamine or a polyethylene glycol chain (Manoharan et al. *Nucleosides & Nucleotides* 1995.14:969), or adamantane acetic acid (Manoharan et al. *Tetrahedron Lett.* 1995.36:3651), a palmityl moiety (Mishra et al. *Biochim. Biophys. Acta* 1995.1264:229), or an octadecylamine or hexylamino-carbonyl-oxycholesterol moiety (Crooke et al. *J. Pharmacol. Exp. Ther.* 1996.277:923). Oligonucleotides comprising lipophilic moieties, and methods for preparing such oligonucleotides, as disclosed in U.S. Pat. Nos. 5,138, 045, 5,218,105 and 5,459,255, the contents of which are hereby incorporated by reference in their entirety.

In other examples the compound to be detected may be a ligand conjugated oligomeric compound having improved pharmacokinetic properties. Such oligomeric compounds are prepared having covalently attached ligands or proteins that bind reversibly to or interact with one or more serum, vascular or cellular proteins. This reversible binding is expected to decrease urinary excretion, increase serum half life and greatly increase the distribution of oligomeric compounds thus conjugated. The binding of particular drugs to plasma protein has been previously shown to enhance the disposition and efficacy of drugs (Herve et al. *Clin. Pharmacokinet.* 1994.26:44).

Many drugs reversibly bind to plasma proteins. A representative list, which is not meant to be inclusive, includes: aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, benzothiadiazides, chlorothiazide, diazepines (such as for example fludiazepam and diazepam) indomethacin, barbiturates (such as for example quinalbarbitone), cephalosporins, sulfa drugs, antidiabetics (such as for example tolbutamide), antibacterials (such as for example a group of quinolones; nalidixic acid and cinoxacin) and several antibiotics. Serum albumin is the most important protein among all plasma proteins for drug binding, although binding to other proteins (for example, macroglobulin G2, immunoglobulins, lipoproteins, alpha-1-acid glycoprotein, thrombin) is also important.

Ligands such as the above drugs that bind serum, vascular or cellular proteins may be attached via an optional linking moiety to one or more sites on an oligonucleotide to be administered to a subject and detected in accordance with the present invention. These sites include one or more of, but are not limited to, the 2'-position, 3'-position, 5'-position, the internucleotide linkage, and a nucleobase atom of any nucleotide residue. The attachment of ligands to such structures can be performed, according to some preferred embodiments of the invention, using a linking group, or without the use of such a linking group. Example linking groups include, 6-aminoalkoxy linkers, 6-aminoalkylamino linkers, cysteamine, heterobifunctional linkers, homobifunctional linkers, and a universal linker (derived from 3-dimethoxytrityloxy-2-aminopropanol). A particularly preferred linking group for the synthesis of ligand conjugated oligonucleotides of the invention is a 6-aminohexyloxy group. A variety of heterobifunctional and homobifunctional linking moieties are available from Pierce Co. (Rockford, Ill.). Such heterobifunctional and homobifunctional linking moieties are particularly useful in conjunction with the 6-aminoalkoxy and 6-aminoalkylamino moieties to form extended linkers useful for linking ligands to a nucleoside. Further useful linking groups that are commercially available are 5'-Amino-Modifier C6 and 3'-Amino-Modifier reagents, both available from Glen Research Corporation (Sterling, Va.). 5'-Amino-Modifier C6 is also available from ABI (Applied Biosystems Inc., Foster City, Calif.) as Aminolink-2, while the 3'-Amino-Modifier is also available from Clontech Laboratories Inc. (Palo Alto, Calif.). In addition, a nucleotide analog bearing a linking group preattached to the nucleoside is commercially available from Glen Research Corporation under the trade name "Amino-Modifier-dT." This nucleoside-linking group reagent, a uridine derivative having an [N(7-trifluoroacetylaminoheptyl)3-acrylamido] substituent group at the 5 position of the pyrimidine ring, is synthesized as per the procedure of Jablonski et al. (*Nucleic Acid Research*, 1986, 14:6115).

Ligand conjugated oligonucleotides may be synthesized by the use of an oligonucleotide that bears a pendant reactive functionality such as that derived from the attachment of a linking molecule onto the oligonucleotide. This reactive oligonucleotide may be reacted directly with commercially available ligands, ligands that are synthesized bearing a variety of protecting groups, or ligands that have a linking moiety attached thereto.

The oligonucleotides detectable in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is well known to use similar techniques to prepare oligonucleotides such as the phosphorothioates and 2'-alkoxy or 2'-alkoxyalkoxy derivatives, including 2'-O-methoxyethyl oligonucleotides (Martin, P., *Helv. Chim. Acta*, 1995, 78, 486-504). It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other conjugated oligonucleotides.

By the terms "administered" or "administered" is meant providing to a subject a modified oligonucleotide. Administration may be topical (including ophthalmic, vaginal, rectal, intranasal, epidermal and transdermal), oral or parenteral, needle injection, needle-free injection as in, for example, an injection using a device like the Medi-Jector™, and by aliquots using a pipette. Parenteral administration includes intravenous drip or infusion, subcutaneous, intraperitoneal or intramuscular injection, pulmonary administration, e.g., by inhalation or insufflation, or intracranial, e.g., intrathecal or intraventricular, administration. Modes of administering oligonucleotides are disclosed in U.S. Pat. No. 6,083,923, the entire contents of which are incorporated herein by reference.

Formulations for topical administration may include transdermal patches, ointments, lotions, creams, gels, drops, suppositories, sprays, liquids and powders.

Compositions for oral administration include powders or granules, suspensions or solutions in water or non-aqueous media, capsules, sachets or tablets. Thickeners, flavoring agents, diluents, emulsifiers, dispersing aids or binders.

Compositions for parenteral administration may include sterile aqueous solutions which may also contain buffers, diluents and other suitable additives. Methods for providing a compound to a subject are well known and are not considered limiting aspects of the present invention. Furthermore, the site or target of administration is also not considered a limiting aspect to the present invention.

"Subject" as used herein refers to a mammal that has been administered a modified oligonucleotide. Non-limiting examples of mammals of the invention include rodent, lagomorph, porcine, canine, feline, and primate. In a preferred embodiment the mammal is a primate and most preferably the mammal is a human.

As used herein "detect" or "detected" means the instrumental measurement or visual observation of the detectable label as indicative of the presence of the synthetic modified oligonucleotide in the obtained bodily fluid and/or extract sample.

By the phrase "obtain(ing) a sample" is meant the extraction or separation of a bodily fluid and/or extract from the subject. Approaches for obtaining, extracting, excising, lancing, dissecting, excreting, evacuating bodily fluid and/or extracts from a subject or by a subject, are well known and have been practiced or requested by nurses, physicians and research scientists. The approach used to obtain the bodily fluid and/or extract is not considered a limiting aspect of the present invention.

In the context of the present invention "bodily fluid and/or extract" refers to any bodily substance removed from the subject to be screened for the presence of an oligonucleotide. While it is understood that some portions of the body are not readily assayed as a fluid, procedures to homogenize and prepare liquid samples from those portions are not uncommon, and are well known. The addition of water or saline to body portions which are normally not liquid is within the scope of the present invention, for example, a homogenized sample of a bone suspension, can be assayed by the methods described herein. Thus, the bodily fluid and/or extract may be prepared, or may be selected from, but not limited to, the following; tissue, bone or organ samples, serum, saliva, feces, tears, sweat, and samples of blood cells, epithelial cells, and the like.

By "probe" is meant an oligonucleotide or polynucleotide configured and arranged to bind the target modified oligonucleotide molecule that has been administered to the subject. Preferably, the probe sequence is substantially complementary to at least a portion of the target nucleic acid sequence and is configured to contain a detectable marker. A "capture probe" is a probe containing a moiety for binding to a solid support, such as biotin, which binds strongly and specifically to streptavidin-coated solid supports such as beads, culture dishes or 96 well plates, for example, allowing "capture" of the oligonucleotide to be detected onto a solid support.

"Detectable marker" as used herein refers to that component or moiety attached to a probe or a component of the probe, which is capable of interacting with and/or binding, directly or indirectly, to a detectable label. In nonlimiting examples, detectable markers include nucleic acids conjugated to a member of a binding pair or substrates for enzymatic reactions such as digoxigenin or a series of nucleotides of known (homogeneous or heterogeneous) sequence, e.g. polyA.

By the term "detectable label" is meant a compound and/or molecule that is observable by either visual or mechanical means. In nonlimiting examples, bifluoro-chromophores, radioactive isotopes, chemiluminescent or chromogenic labels presently available may be used as detectable labels. The detectable label and the manner by which the label is monitored are not considered to be limiting factors of the present invention. The detectable label can be part of a binding pair such as for example biotin-streptavidin, digoxigenin conjugated to alkaline phosphatase or other antigen-antibody complexes. The detectable label offers a way to determine the presence of the modified oligonucleotide via positive interaction with the probe.

The following examples illustrate aspects the present invention and are not intended to limit the same. Although the examples presented below relate to detection of particular oligonucleotides using the methods of the present invention, any oligonucleotide having a known sequence may be detected using a probe which has a complementary sequence.

Example 1

Oligonucleotide Detection Assay Method

The desired volume of oligonucleotide (analyte)-containing plasma (100 µl) was aliquoted into 96-well plates. To every 100 µL of human or monkey plasma, 5 (L of 10% NP-40 was added.

Plasma standard curve and quality control (QC) samples were prepared as follows. Equivalent volumes of control blank plasma (90 µL) from untreated animals or humans were aliquoted into the appropriate number of wells as specified below. Ten µL of the appropriate concentration of oligonucleotide were added to the plasma on the plate as specified below. Calibration standards and QC samples were distributed evenly among the study samples. A minimum of six non-zero concentrations in duplicate bracketing the expected concentration range of unknown samples were used as standard curve points. The analyte oligonucleotide was added to plasma to achieve the desired concentrations. Three concentrations of QC standard were prepared (low, medium and high) in at least duplicate. The low QC was near the limit of quantitation (LOQ) concentration (i.e., (3×LOQ). The medium QC was about midway between the high and low QC concentrations. The high QC was at 75 to 90% of the highest calibration standard. A minimum of three matrix blanks and two water blanks was run with each plate of sample analysis. The plate was vortexed on an Ambi-Hi-Lo incubator (VWR Scientific) for about 5 seconds to mix.

To the plasma samples, calibration standard, QC samples and blanks, 100 µL of Cutting Probe Working Solution (0.05 µM template probe complementary to the analyte in 60 mM Na2HPO4, pH 7.4, 0.9 M NaCl, 0.24% Tween-20) was added and the plate was incubated at 37° C. for one hour. The 3'-end of the probe is biotinylated and the 5'-end is labeled with digoxigenin (Operon Technologies, Inc.). 150 µL of this hybridization solution was transferred onto Reacti-Bind™ NeutrAvidin Coated Polystyrene Strip Plates (Clear) (Pierce Chemical Co.) using a multi-channel pipette, and the plate was incubated at 37° C. for 30 minutes. After incubation, the plate was refrigerated (4-8° C.) for about 10 minutes. The plate was then washed four times with 1×TBS/Tween (25 mM Tris-HCl, pH 7.2, 0.15 M NaCl, 0.1% Tween-20).

To each well was added 300 µL S1 nuclease solution (50 units/mL of S1 nuclease (Life Technologies) in 30 mM sodium acetate, pH 4.6, 1 mM ZnCl2, 5% (v/v) glycerol, and the plate was incubated at room temperature for two hours, then washed four times with 1×TBS/Tween. Anti-digoxigenin-alkaline phosphatase (AP) working solution (1:2000 dilution of Anti-digoxigenin-AP, Fab fragments (Boehringer Mannheim). (150 µL) was added to each well and the plate was incubated at room temperature for 30 minutes. The wells were then washed five times with 1×TBS/Tween. ATTOPHOS Working Solution (60 mL of ATTOPHOS reconstitution solution (JBL Scientific) mixed with 36 mg ATTOPHOS(fluorescent substrate (JBL Scientific)). 150 µL was added at 10 second increments per row/column. The plate was incubated at 37° C. for 10-20 minutes until fluorescence of the most concentrated calibration point reached 18000-23000 at 45 gain. Stop solution (70 µL of 25% Na$_2$HPO$_4$.7H$_2$O in water (w/v)) was then added at 10 second increments per row/column in the same order as was the ATTOPHOS solution. The plate was read in a fluorescence plate reader (CytoFluor) with the excitation set at 450/50 and the emission at 580/80 at gain of 45 and 42.

Example 2

Selectivity for Metabolites

Figure 3:
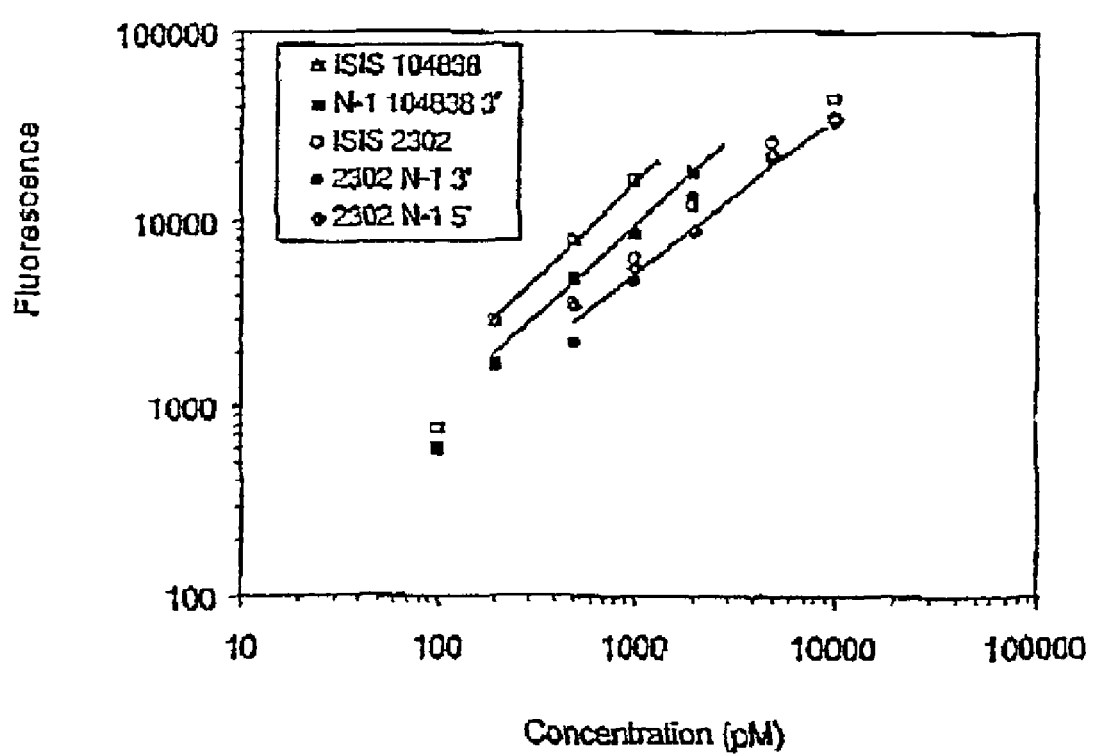
FIG. 3 is a graph comparing different antisense oligonucleotides. ISIS 104838: 5'-GCTGATTAGAGAGAGGTCCC-3' (SEQ ID NO:1); ISIS 2302: GCCCAAGCTGGCATC-CGTCA (SEQ ID NO:2); N-1 104838 3': ISIS 104838 metabolite shortened by one nucleotide at the 3'-end; 2302 N-1 3': ISIS 2302 metabolite shortened by one nucleotide at the 3'-end; 2302 N-1 5': 2302 shortened by one nucleotide at the 5'-end. ISIS 104838 has a 2'-O-methoxyethyl ribose at positions 1-5 and 16-20, and all internucleoside linkages are phosphorothioates.

A plate was prepared and concentrations of the following metabolites were measured by the method described in Example 1: N-1 from the 3'-end of ISIS 104838, N-1 from the 3'-end of ISIS 2302 and N-1 from the 5'-end of ISIS 2302. Full-length ISIS 2302 and 104838 were also measured. The results are shown in FIG. 3. All oligonucleotides were detected by the method and produced linear results, although the response for the metabolites was slightly less. Thus, the assay is not selective to metabolites or full length oligonucleotide.

Example 3

Detection of 2'-MOE Oligonucleotides

Figure 4:
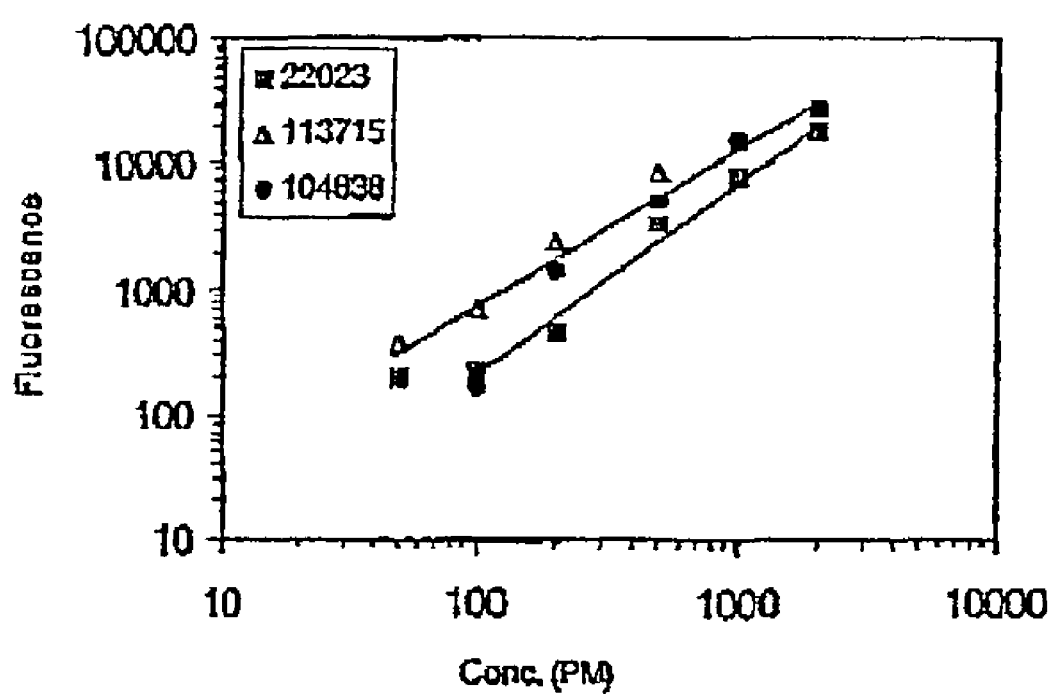
FIG. 4 is a graph comparing different modified antisense oligonucleotides which contain methoxyethyl (MOE) modifications at the 2' position of the ribose sugar. 22023=5'-TCCAGCACTTTCTTTTCCGG-3' (SEQ ID NO: 3); 113715=5'-GCTCCTTCCACTGATCCTGC-3' (SEQ ID NO: 4). ISIS 22023 and ISIS 113715 have a 2'-O-methoxyethyl ribose at positions 1-5 and 16-20, and all internucleoside linkages are phosphorothioates.

Concentrations of the following 2'-methoxyethyl (2'-MOE) were measured by the method describe in Example 1: ISIS 104838 (SEQ ID NO: 1), ISIS 22023 (SEQ ID NO: 3) and ISIS 113715 (SEQ ID NO:4). Complementary oligonucleotide probes labeled at the 3'-end with digoxigenin and the 5'-end with biotin were used to detect each analyte. The results are shown in FIG. 4. All three oligonucleotides showed linearity.

Example 4

Validation of ISIS 22023 in Mouse Plasma

ISIS 22023 was added to mouse plasma to obtain concentrations of 50 pM, 100 pM, 500 pM and 1500 pM. To validate the assay, the protocol described in Example 1 was used to quantitate ISIS 22023 at each of these concentrations. Six replicates of each concentration were analyzed. The results are shown in Table 1. The assay showed good accuracy and precision. The "mean" column indicates the mean concentration of oligonucleotide determined by the assay for the six replicates.

TABLE 1

| ID | Nominal conc., pM | Mean | SD | Accuracy | % relative SD (RSD) |
|---|---|---|---|---|---|
| LOQ | 50 | 52 | 49 | 103.4 | 19.2 |
| Low QC | 10 | 85 | 15 | 84.9 | 17.9 |
| Mid QC | 500 | 571 | 63 | 114.2 | 11.0 |
| High QC | 1500 | 1661 | 158 | 110.7 | 9.5 |

Example 5

Figure 5:
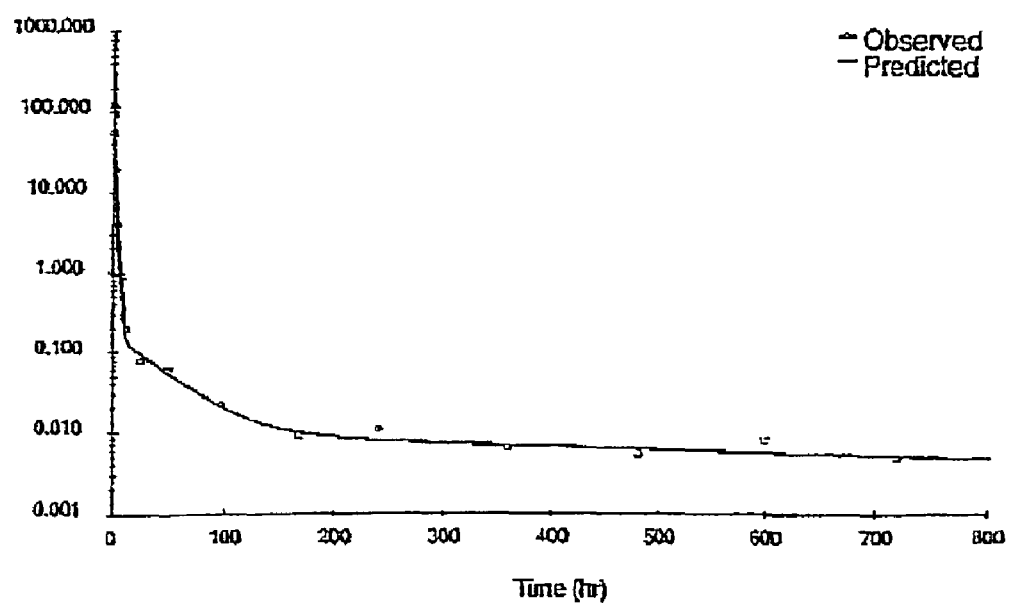
FIG. 5 is a graph showing the pharmacokinetic profile of ISIS 22023 following 50 mg/kg subcutaneous injection in mice. Plasma samples were analyzed at various time points using the oligonucleotide detection method of the present invention.

Detection of ISIS 22023 after injection in mice ISIS 22023 (50 mg/kg) was injected subcutaneously into mice and the plasma concentration was determined at various times post-injection by the method described in Example 1. The results are shown in FIG. 5. ISIS 2302 had a very long elimination half-life. The predicted and observed half lives corresponded very well.

Example 6

ISIS 104838 Stability Studies

Multiple storage vials containing ISIS 104838 at concentrations of 100 pM, 500 pM and 1500 pM were prepared in monkey plasma and stored at −80° C. To determine freeze-thaw stability, replicates at each concentration were studied after cycles of 1 and 3 freeze-thaws. For determination of short-term room temperature stability, replicates at each concentration were kept at room temperature for 24 hours. The results (Tables 2 and 3; F-T=freeze-thaw) show that ISIS 104838 appeared stable for 24 hours at room temperature in monkey plasma, was stable for 1 day at −80° C., and were stable through freeze-thaw cycles. Results were consistent among freeze-thaw samples and 10-day storage samples.

TABLE 2

| ID | Storage Time | Conc., pM | Accuracy | % RSD |
|---|---|---|---|---|
| Low QC | 24 hr, RT | 100 | 157.9 | 21.31 |
| Medium QC | 24 hr, RT | 500 | 124.6 | 6.58 |
| High QC | 24 hr, RT | 1500 | 96.3 | 7.12 |
| Low QC | 1 F-T | 100 | 109.9 | 18.90 |
| Medium QC | 1 F-T | 500 | 119.1 | 7.00 |
| High QC | 1 F-T | 1500 | 92.9 | 7.60 |

TABLE 3

| ID | Storage Time | Conc., pM | Calc. Conc., pM | Accuracy | % RSD |
|---|---|---|---|---|---|
| Low QC | 3 F-T | 100 | 168 | 167.6 | 15.38 |
| Medium QC | 3 F-T | 500 | 672 | 134.3 | 3.98 |
| High QC | 3 F-T | 1500 | 1516 | 101.0 | 1.76 |
| Low QC | 10 day freezer | 100 | 164 | 164.2 | 13.5 |
| Medium QC | 10 day freezer | 500 | 715 | 143.0 | 22.89 |
| High QC | 10-day freezer | 1500 | 1545 | 103.0 | 5.01 |

Example 7

Stability of ISIS 104838 in Human Plasma

ISIS 104838 was stored at about 20° C. and protected from light. The purity of the reference standard was measured by capillary gel electrophoresis and was found to be 99.807%. All samples were analyzed using cutting assay described in Example 1. A calibration curve for ISIS 104838 in human plasma was determined and the results are presented in Table 4 below.

TABLE 4

| Conc, pM | Fluorescence | | Calculated Conc, pM | | % Accuracy | % Accuracy |
|---|---|---|---|---|---|---|
| | Curve 1 | Curve 2 | Curve 1 | Curve 2 | Curve 1 | Curve 2 |
| Ave. Blk | 1001 | | | | | |
| 100 | 1512 | 1604 | 84 | 89 | 84 | 89 |
| 200 | 3534 | 3780 | 211 | 227 | 105 | 113 |
| 500 | 8861 | 9012 | 570 | 581 | 114 | 116 |
| 1000 | 14991 | 16310 | 1009 | 1105 | 101 | 111 |
| 1500 | 20481 | 21973 | 1415 | 1527 | 94 | 102 |
| 2000 | 24519 | 26010 | 1719 | 1838 | 86 | 92 | b[0] 1.4048
b[1] 0.9225 Regression 1 passed.
$r^2$ 0.9897

Figure 6:
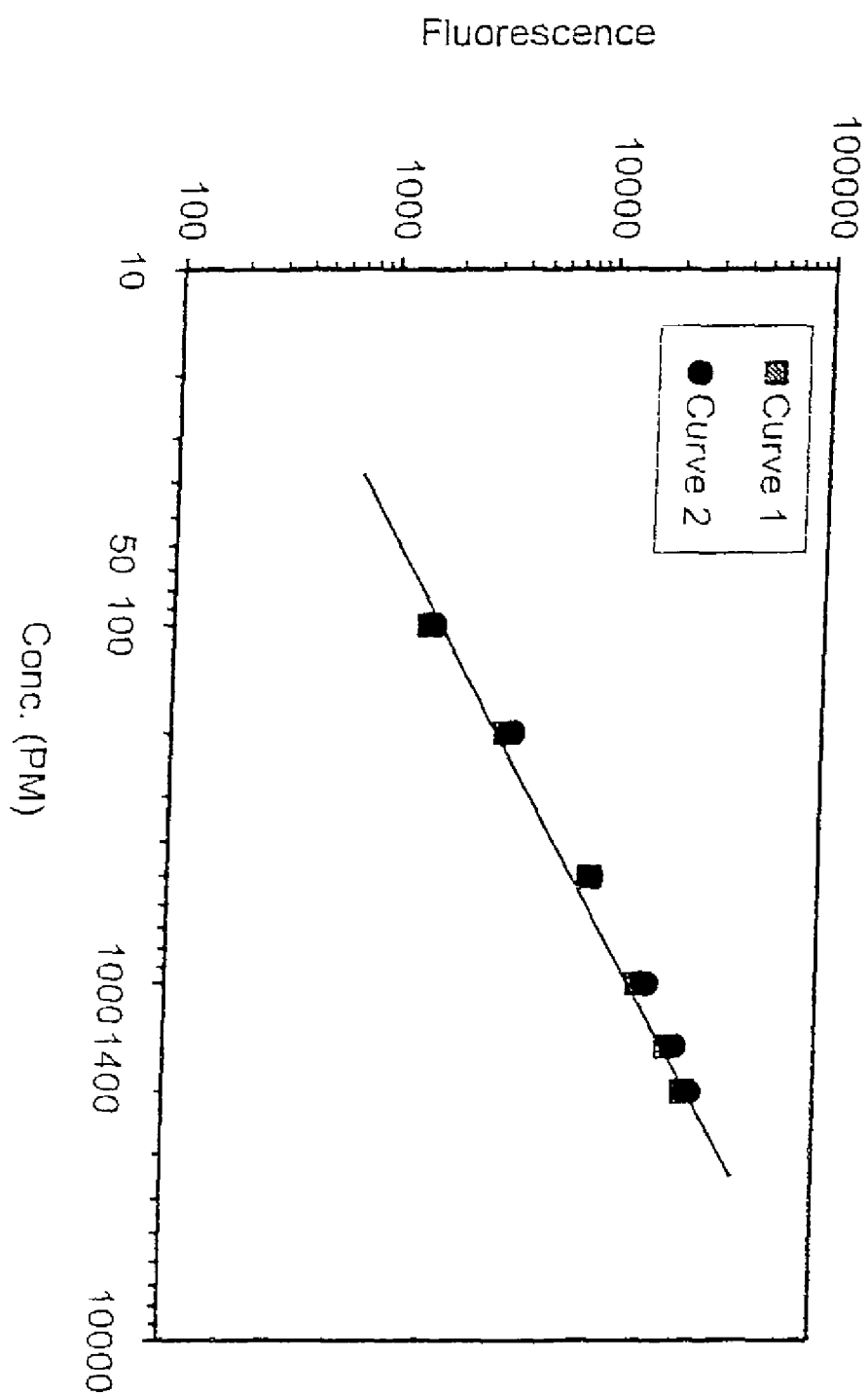
FIG. 6 is a representative calibration curve of ISIS 104838 in human plasma from 100 pM to 2000 pM using the oligonucleotide detection method of the present invention. The calibration points included 100, 200, 500, 1000, 1500 and 2000 picomolar concentrations. Each calibration point was run in duplicate. From this curve, responses for concentrations other than the calibration points can be extrapolated. It can be seen that concentrations between 50 and 1400 picomolar are detected.

FIG. 6 is a representative calibration curve of ISIS 104838 in human plasma from 100 pM to 2000 pM using the oligonucleotide detection method of the present invention. The calibration points included 100, 200, 500, 1000, 1500 and 2000 picomolar concentrations. Each calibration point was run in duplicate. From this curve, responses for concentrations other than the calibration points can be extrapolated. It can be seen that concentrations between 50 and 1400 picomolar are detectable.

Stability of ISIS 104838 in human plasma was studied at nominal values of low (300 pM), medium (750 pM) and high (1500 pM) oligonucleotide concentrations. The actual concentrations determined right after sample preparation were 369, 901 and 1857 pM for low, medium and high, respectively. Room temperature, freeze/thaw and long term freezer storage stability were performed. The samples were stable stored at 1 and 24 hr at room temperature (81.3-122.7 of expected concentrations) at all the concentrations examined (Table 5). Following freezer storage at −70° C. for 7 days, the samples were also stable (83.9-104.9% of expected concentrations) (Table 6). Following one freeze/thaw cycle, the observed concentration at 369 pM was 52.2% higher than the expected concentration and the observed concentration was in the range of 99.5-120% of expected concentrations at 901 and 1857 pM (Table 7).

TABLE 5

| Storage time | Conc. Spiked (pM) | Observed conc. (mean ± SD) | % Nominal | % CV |
|---|---|---|---|---|
| 1 hr | 369 | 300 ± 14 | 81.3 | 4.52 |
| | 901 | 775 ± 31 | 86.0 | 3.97 |
| | 1857 | 1507 ± 45 | 81.2 | 3.01 |
| 24 hr | 369 | 453 ± 23 | 122.7 | 5.15 |
| | 901 | 908 ± 29 | 100.7 | 3.22 |
| | 1857 | 1582 ± 50 | 85.2 | 3.16 |

TABLE 6

| Conc. Spiked (pM) | Observed conc. (pM) (mean ± SD) | % Nominal | % CV |
|---|---|---|---|
| 369 | 387 ± 29 | 104.9 | 7.56 |
| 901 | 810 ± 125 | 89.8 | 15.4 |
| 1857 | 1558 ± 90 | 83.9 | 5.81 |

TABLE 7

| Conc. Spiked (pM) | Observed conc. (pM) (mean ± SD) | % Nominal | % CV |
|---|---|---|---|
| 369 | 561 ± 43 | 152.2 | 7.57 |
| 901 | 1082 ± 77 | 120.0 | 7.16 |
| 1857 | 1847 ± 44 | 99.5 | 2.38 |

Example 8

Specificity

Control human plasma from ten subjects was analyzed in triplicate for possible endogenous interference. As shown in Table 6, plasma from all subjects had a response less than 50% of the response at the LOQ (100 pM). A linear range of 100 pM (0.1 nM) to 20,000 pM (20 nM) (r≧0.98) was obtained in human plasma for ISIS 104838. Therefore, no interference was noted from the human plasma.

TABLE 8

| Subject # | Calc. Conc. (pM) Equivalent to ISIS 104838 (Mean ± SD) | % LOQ |
|---|---|---|
| 1 | 4594 ± 1.32 | 45.94 |
| 2 | 50.89 ± 0.64 | 50.89 |
| 3 | 47.92 ± 4.65 | 47.92 |
| 4 | 44.85 ± 2.81 | 44.85 |
| 5 | 46.58 ± 3.61 | 46.58 |
| 6 | 37.47 ± 5.71 | 37.47 |
| 7 | 40.65 ± 2.66 | 40.65 |
| 8 | 42.18 ± 2.12 | 42.18 |
| 9 | 41.28 ± 2.72 | 41.28 |
| 10 | 37.54 ± 1.38 | 37.54 |

Example 9

Calibration Curves

Figure 7:
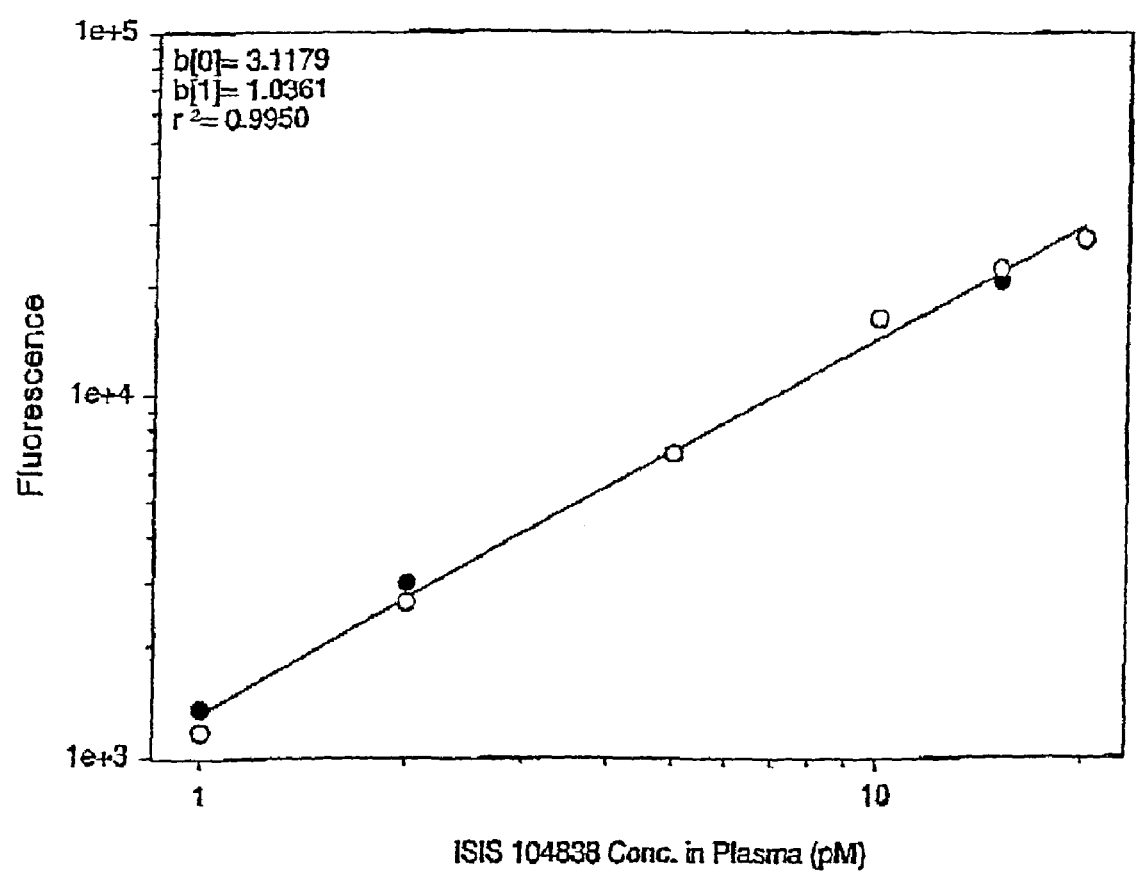
FIG. 7 is a representative calibration curve of ISIS 104838 in human plasma from 1 nM to 20 nM using the oligonucleotide detection method of the present invention. Each calibration point was run in duplicate.

Calibration curves (100 to 2000 pM) and 1 to 20 nM) in human plasma were run by two analysts on three different days. Each calibration curve was run in duplicate at concentrations of 100, 200, 500, 1000, 1500, and 2000 pM for the low curve, and 1, 2, 5, 10, 15, 20 nM for the high curve. Each curve was fitted to log/log linear curve without weighting. Representative high and low calibration curves are shown in FIGS. 6 and 7, respectively. Correlation coefficients for ISIS 104838 were found to be greater than or equal to 0.98 for all calibration curves. Therefore, an acceptable linearity was achieved at concentrations from 100 pM to 20 nM for ISIS 104838 in human plasma.

Example 10

Intra-Day Accuracy and Precision

Six replicate QC samples at four concentrations were used to evaluate intra-day accuracy and precision. The concentrations evaluated were LOQ (100 pM), low (300 pM), medium (750 pM), high (1500 pM) QC and dilution QC (10,000 pM, dilution 1:10) samples performed in human plasma. A 1:10 dilution with blank human plasma was made for the dilution QC sample prior to sample analysis. Intra-day analysis was performed on three different days by two different analysts. Concentrations of ISIS 104838 from the LLOQ, low, medium, high and diluted QC samples were analyzed using the following calibration curve method (Equation 1)

$$\text{Log}_{10}(C_2) = \text{Log}_{10}(\text{Flu}) - \text{intercept/slope} \quad (1)$$

Where $C_2$=concentration of the analyte (ISIS 104838), Flu=fluorescence reading of the analyte, intercept and slope were from linear regression of the calibration curve. Accuracy for the QC samples was calculated as the percentage of the calculated concentrations compared to the nominal concentrations for ISIS 104838 (% Actual). Precision was expressed as coefficient of variation (% CV). The results for Days 1 to 3 intra-day accuracy are shown in Tables 9a-9c, respectively.

TABLE 9a

| ID | Nominal conc. (pM) | Calc. Conc. (pM) (mean ± SD) | % Actual | % CV |
|---|---|---|---|---|
| LOQ | 100 | 91 ± 14 | 90.8 | 15.1 |
| Low QC | 300 | 353 ± 28 | 117.7 | 8.1 |
| Mid QC | 750 | 839 ± 52 | 111.8 | 6.2 |
| High QC | 1500 | 1456 ± 37 | 97.1 | 2.5 |
| Dilution QC | 10000 | 10215 ± 631 | 102.2 | 6.2 |

TABLE 9b

| ID | Nominal conc. (pM) | Calc. Conc. (pM) (mean ± SD) | % Actual | % CV |
|---|---|---|---|---|
| LOQ | 100 | 82 ± 11 | 81.6 | 13.7 |
| Low QC | 300 | 310 ± 30 | 103.4 | 9.8 |
| Mid QC | 750 | 793 ± 71 | 105.7 | 8.9 |
| High QC | 1500 | 1486 ± 92 | 99.1 | 6.2 |
| Dilution QC | 10000 | 9893 ± 496 | 98.9 | 5.0 |

TABLE 9c

| ID | Nominal conc. (pM) | Calc. Conc. (pM) (mean ± SD) | % Actual | % CV |
|---|---|---|---|---|
| LOQ | 100 | 93 ± 20 | 93.3 | 21.8 |
| Low QC | 300 | 223 ± 36 | 74.4 | 16.2 |
| Mid QC | 750 | 741 ± 149 | 98.8 | 20.1 |
| High QC | 1500 | 1584 ± 173 | 105.6 | 10.9 |
| Dilution QC | 10000 | 9364 ± 1758 | 93.6 | 18.8 |

Acceptable assay accuracy was achieved for LOQ, low, mid, high and dilution QC (in the range of 90.8-117.7% of nominal spiked concentrations on Day 1, 81.6-105.7% on Day 2, 93.3-105.6% on Day 3) with the exception of the low QC on Day 3, where the % Actual was 74.4%. Therefore, the accuracy acceptance criteria was generally met (75-125% at LOQ and 80-120% at other QC levels). Acceptable intra-day precision (expressed as coefficient of variation, % CV) was less than 21.8% and less than 20.1% for LOQ and QC samples, respectively, which met the acceptance criteria (<25% at LOQ and <20% at other QC levels).

Example 11

Inter-Day Precision and Accuracy

Inter-day accuracy and precision were calculated from the pooled data of QC using 18 replicates of QC samples each at five different concentrations (100, 300, 750, 1500 and 10,000 pM) performed on three different days by two analysts. Acceptable inter-day assay accuracy was achieved for the quantitation of ISIS 104838 (in the range of 88.6%-105.5% of nominal spiked concentrations over the concentration range studied) (Table 10). Acceptable inter-day assay precision was also obtained (% CV≦21.4%), which met the precision acceptance criteria. The dilution QC had an inter-day accuracy at 98.2% with % CV of 11.3%, which met the precision acceptance criteria. The inter-day data showed that the method was reproducible in different days and across multiple analysts.

TABLE 10

| ID | Nominal conc. (pM) | Calc. Conc. (pM) (mean ± SD) | % Actual | % CV |
|---|---|---|---|---|
| LOQ | 100 | 89 ± 16 | 88.6 | 17.5 |
| Low QC | 300 | 296 ± 63 | 98.5 | 21.4 |
| Mid QC | 750 | 791 ± 102 | 105.5 | 12.9 |
| High QC | 1500 | 1509 ± 122 | 100.6 | 8.1 |
| Dilution QC | 10000 | 9824 ± 1109 | 98.2 | 11.3 |

Example 12

Cross-Validation to High Range in Human Plasma

In order to determine samples at higher calibration range, a one-day cross-validation at a high range was conducted. In this validation procedure, a six-point calibration standard from 1 nM to 20 nm (at 1, 2, 5, 10, 15 and 20 nM) in duplicate was prepared and analyzed by the cutting assay described in Example 1. Accuracy and precision were assessed with QC samples in six replicates at 2 nM (LLOQ), 5 nM (low QC), 10 nM (medium QC) and 15 nM (high QC) prepared in human plasma. To verify the accuracy and precision of dilution samples, an extra high QC sample (containing 1000 nM of ISIS 104838) in human plasma was prepared in six replicates. A 1:100 dilution with blank human plasma was made for this QC sample prior to sample analysis. For sample preparation of the calibration standards and QC samples, 12.5 µl of standard solution was spiked into 12.5 µl of human plasma and 100 µl of distilled water.

The linear range for the high curve was 1 to 20 nM with r2≧0.98. As shown in Table 11, the accuracy and precision for the LOQ, low, medium and high QC had an % Actual in the range of 108.3-119.1% with % CV≦10.0%, which met the established accuracy and precision acceptance criteria. The dilution QC had an accuracy of 117.4% with % CV of 6.4%, which also met the accuracy and precision acceptance criteria. In summary, the cross-validation to a high calibration range indicated that the assay was accurate and precise for the quantitation of ISIS 104838 at concentrations between 1 and 20 nM with dilution samples up to 1000 nM (1 µM) in human plasma.

TABLE 11

| ID | Nominal conc. (nM) | Calc. Conc. (nM) (mean ± SD) | % Actual | % CV |
|---|---|---|---|---|
| LOQ | 2 | 2.27 ± 0.23 | 113.6 | 10.0 |
| Low QC | 5 | 5.77 ± 0.27 | 115.3 | 4.7 |
| Mid QC | 10 | 11.91 ± 0.70 | 119.1 | 5.9 |
| High QC | 15 | 16.24 ± 0.37 | 108.3 | 2.3 |
| Dilution QC | 1000 | 1174 ± 75 | 117.4 | 6.4 |

In summary, the assay was specific, accurate, precise and sensitive for the quantitation of ISIS 104838 in human plasma. Moreover, the method was reproducible by multiple analysis.

What is claimed is:

1. A method for detecting or quantitating an oligonucleotide in a bodily fluid or extract wherein the oligonucleotide is 8 to 50 nucleosides in length, comprising:
   creating a test sample by contacting the bodily fluid or extract with a probe, wherein:
      the probe is complementary to the oligonucleotide; and
      the probe comprises a detectable marker and a binding moiety, wherein the detectable marker and the binding moiety are each covalently bound to the probe;
   contacting the test sample with a solid support wherein the solid support comprises a binding partner of the binding moiety;
   contacting the test sample with a single-strand-specific nuclease;
   washing the test sample to remove detectable marker that is not associated with the solid support;
   detecting the presence or amount of detectable marker in the test sample; and
   thereby detecting or quantitating the oligonucleotide in the bodily fluid or extract.

2. The method of claim 1 wherein the oligonucleotide is 20-30 nucleosides in length.

3. The method of claim 1 wherein the bodily fluid is plasma.

4. The method of claim 1 wherein the oligonucleotide comprises at least one phosphorothioate linkage.

5. The method of claim 1 wherein the oligonucleotide comprises at least one 2' sugar modification.

6. The method of claim 5 wherein the 2' sugar modification is a 2'-O-methoxyethyl modification.

7. The method of claim 5 wherein the oligonucleotide is a gapmer.

8. The method of claim 5 wherein the oligonucleotide is a hemimer.

9. The method of claim 1 wherein the oligonucleotide comprises at least one modified base.

10. The method of claim 9 wherein the modified base is 5-methylcytosine.

11. The method of claim 1 wherein detecting the detectable marker comprises detecting a detectable label selected from among a colorimetric, radioactive, chemiluminescent, enzymatic or fluorescent label.

12. The method of claim 1 wherein the detectable label is digoxigenin.

13. The method of claim 1 wherein the single-strand-specific nuclease is S1 nuclease.

14. The method of claim 1 wherein the single-strand-specific nuclease is mung bean nuclease.

* * * * *